United States Patent
Bhalay et al.

(10) Patent No.: US 7,034,042 B2
(45) Date of Patent: *Apr. 25, 2006

(54) N-(4-ARYLOXYPIPERIDIN-1-YLALKYL) CINNAMIC AMIDES AS CCR33 RECEPTOR ANTAGONISTS

(75) Inventors: Gurdip Bhalay, Horsham (GB); Trevor J Howe, Horsham (GB); Darren M Le Grand, Horsham (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/398,533

(22) PCT Filed: Oct. 8, 2001

(86) PCT No.: PCT/EP01/11627

§ 371 (c)(1),
(2), (4) Date: Apr. 8, 2003

(87) PCT Pub. No.: WO02/30898

PCT Pub. Date: Apr. 18, 2002

(65) Prior Publication Data

US 2004/0087621 A1    May 6, 2004

(30) Foreign Application Priority Data

Oct. 9, 2000  (GB)  .................... 0024675
Aug. 23, 2001 (GB)  .................... 0120549

(51) Int. Cl.
*A61K 31/445* (2006.01)
*C07D 211/22* (2006.01)

(52) U.S. Cl. ............. 514/327; 514/235.5; 514/253.12; 514/326; 544/129; 544/360; 546/216; 546/210; 546/221

(58) Field of Classification Search ................ 546/221, 546/216, 210; 544/129, 360; 514/326, 327, 514/235.5, 253.12
See application file for complete search history.

(56) References Cited

U.S. PATENT DOCUMENTS

| 4,673,684 A | 6/1987 | Wakabyashi et al. | ....... 514/327 |
| 4,795,752 A | 1/1989 | Hattori et al. | ............... 514/327 |
| 6,670,379 B1 * | 12/2003 | Howe et al. | ................ 514/330 |

FOREIGN PATENT DOCUMENTS

| DE | 197 56 235 | 7/1999 |
| EP | 0 399 569 | 11/1990 |
| JP | 63 179869 | 7/1988 |
| WO | 88/04169 | 6/1988 |
| WO | 00/58305 | 10/2000 |

OTHER PUBLICATIONS

Rollins BJ. Blood. 1997, 90(3): 909-928.*
Hesselgesser et al. J. Biol. Chem. 1996, 273 (25) :15687-15692.*

* cited by examiner

*Primary Examiner*—Celia Chang
(74) *Attorney, Agent, or Firm*—Gregory C. Houghton

(57) ABSTRACT

Compounds of formula (I) in free or salt form, where $Ar^1$ is phenyl substituted by one or more substituents selected from halogen, cyano, nitro, and $C_1$–$C_8$-alkyl optionally substituted by cyano or halogen, $Ar^2$ is phenyl optionally which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl, $R^1$ is $C_1$–$C_8$-alkyl substituted by hydroxy, $C_1$–$C_8$-alkoxy, acyloxy, —$N(R^2)R^3$, halogen, carboxy, $C_1$–$C_8$-alkoxycarbonyl, phenyl-$C_1$–$C_8$-alkoxycarbonyl, —$CON(R^4)R^5$ or by a monovalent cyclic organic group, $R^2$ and R?3 ¿are each independently hydrogen or $C_1$–$C_8$-alkyl, or $R^2$ is hydrogen and $R^3$ is acyl or $SO_2R^6$, or $R^2$ and $R^3$ together with the nitrogen atom to which they are attached denote a 5- or 6-membered heterocyclic group, $R^4$ and $R^5$ are each independently hydrogen, $C_1$–$C_8$-alkyl optionally substituted by hydroxy or phenyl, or phenyl optionally substituted by $C_1$–$C_8$-alkyl, halogen, cyano or $C_1$–$C_8$-alkoxy, or $R^4$ and $R^5$ together with the nitrogen atom to which they are attached denote a 5- or 6-membered heterocyclic group, R?6 ¿is $C_1$–$C_8$-alkyl, $C_1$–$C_8$-haloalkyl, or phenyl optionally substituted by $C_1$–$C_8$-alkyl, and n is 1, 2, 3 or 4. The compounds are useful as pharmaceuticals.

16 Claims, No Drawings

N-(4-ARYLOXYPIPERIDIN-1-YLALKYL) CINNAMIC AMIDES AS CCR33 RECEPTOR ANTAGONISTS

This Application is a 371 of PCT/EP01/11627 filed on Oct. 8, 2001.

This invention relates to organic compounds, their preparation and their use as pharmaceuticals.

In one aspect, the invention provides compounds of formula

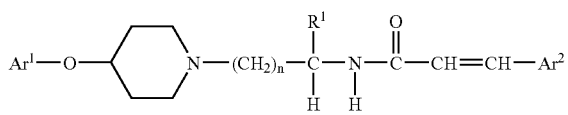

I in free or salt form, where $Ar^1$ is phenyl substituted by one or more substituents selected from halogen, cyano, nitro, and $C_1$–$C_8$-alkyl optionally substituted by cyano or halogen, $Ar^2$ is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl, $R^1$ is $C_1$–$C_8$-alkyl substituted by hydroxy, $C_1$–$C_8$-alkoxy, acyloxy, —N($R^2$)$R^3$, halogen, carboxy, $C_1$–$C_8$-alkoxycarbonyl, phenyl-$C_1$–$C_8$-alkoxycarbonyl, —CON($R^4$)$R^5$ or by a monovalent cyclic organic group, $R^2$ and $R^3$ are each independently hydrogen or $C_1$–$C_8$-alkyl, or $R^2$ is hydrogen and $R^3$ is acyl or —SO$_2$$R^6$, or $R^2$ and $R^3$ together with the nitrogen atom to which they are attached denote a 5- or 6-membered heterocyclic group, $R^4$ and $R^5$ are each independently hydrogen, $C_1$–$C_8$-alkyl optionally substituted by hydroxy or phenyl, or phenyl optionally substituted by $C_1$–$C_8$-alkyl, halogen, cyano or $C_1$–$C_8$-alkoxy, or $R^4$ and $R^5$ together with the nitrogen atom to which they are attached denote a 5- or 6-membered heterocyclic group, $R^6$ is $C_1$–$C_8$-alkyl, $C_1$–$C_8$-haloalkyl, or phenyl optionally substituted by $C_1$–$C_8$-alkyl, and n is 1, 2, 3 or 4.

In one preferred aspect, the invention provides compounds of formula

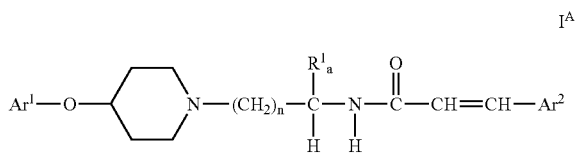

I$^A$ in free or salt form, where $Ar^1$ is phenyl substituted by one or more substituents selected from halogen, cyano, nitro, and $C_1$–$C_8$-alkyl optionally substituted by cyano or halogen, $Ar^2$ is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl, $R^1_a$ is $C_1$–$C_8$-alkyl substituted by hydroxy, $C_1$–$C_8$-alkoxy, acyloxy, —N($R^2$)$R^3$, halogen, carboxy, $C_1$–$C_8$-alkoxycarbonyl, —CON($R^4$)$R^5$ or by a monovalent cyclic organic group, $R^2$ and $R^3$ are each independently hydrogen or $C_1$–$C_8$-alkyl, or $R^2$ is hydrogen and $R^3$ is acyl or —SO$_2$$R^6$, or $R^2$ and $R^3$ together with the nitrogen atom to which they are attached denote a 5- or 6-membered heterocyclic group, $R^4$ and $R^5$ are each independently hydrogen or $C_1$–$C_8$-alkyl, or $R^4$ and $R^5$ together with the nitrogen atom to which they are attached denote a 5- or 6-membered heterocyclic group, $R^6$ is $C_1$–$C_8$-alkyl, $C_1$–$C_8$-haloalkyl, or phenyl optionally substituted by $C_1$–$C_8$-alkyl, and n is 1, 2, 3 or 4.

Terms used in the specification have the following meanings:

"$C_1$–$C_8$-alkyl" as used herein denotes straight chain or branched $C_1$–$C_8$-alkyl, which may be, for example, methyl, ethyl, n-propyl, isopropyl, n-butyl, isobutyl, sec-butyl, tert-butyl, straight or branched pentyl, straight or branched hexyl, straight or branched heptyl, or straight or branched octyl. Preferably, $C_1$–$C_8$-alkyl is $C_1$–$C_4$-alkyl.

"$C_1$–$C_8$-alkoxy" as used herein denotes straight chain or branched $C_1$–$C_8$-alkoxy which may be, for example, methoxy, ethoxy, n-propoxy, isopropoxy, n-butoxy, isobutoxy, sec-butoxy, tert-butoxy, straight or branched pentoxy, straight or branched hexyloxy, straight or branched heptyloxy, or straight or branched octyloxy. Preferably, $C_1$–$C_8$-alkoxy is $C_1$–$C_4$-alkoxy.

"$C_1$–$C_8$-haloalkyl" as used herein denotes $C_1$–$C_8$-alkyl as hereinbefore defined substituted by one or more halogen atoms, preferably one, two or three halogen atoms.

"Acyl" as used herein denotes alkylcarbonyl, for example $C_1$–$C_8$-alkylcarbonyl where $C_1$–$C_8$-alkyl may be one of the $C_1$–$C_8$-alkyl groups hereinbefore mentioned, optionally substituted by one or more halogen atoms; cycloalkylcarbonyl, for example $C_3$–$C_8$-cycloalkylcarbonyl where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyl having one or two hetero atoms selected from nitrogen, oxygen and sulfur in the ring, such as furylcarbonyl or pyridylcarbonyl; arylcarbonyl, for example $C_6$–$C_{10}$-arylcarbonyl such as benzoyl; or aralkylcarbonyl, for example $C_6$ to $C_{10}$-aryl-$C_1$–$C_4$-alkylcarbonyl such as benzylcarbonyl or phenylethylcarbonyl. Preferably acyl is $C_1$–$C_4$-alkylcarbonyl.

"Acyloxy" as used herein denotes alkylcarbonyloxy, for example $C_1$–$C_8$-alkylcarbonyloxy where $C_1$–$C_8$-alkyl may be one of the $C_1$–$C_8$-alkyl groups hereinbefore mentioned, optionally substituted by one or more halogen atoms; cycloalkylcarbonyloxy, for example $C_3$–$C_8$-cycloalkylcarbonyloxy where $C_3$–$C_8$-cycloalkyl may be, for example, cyclopropyl, cyclobutyl, cyclopentyl, cyclohexyl, cycloheptyl or cyclooctyl; 5- or 6-membered heterocyclylcarbonyloxy having one or two hetero atoms selected from nitrogen, oxygen and sulfur in the ring, such as furylcarbonyloxy or pyridylcarbonyloxy; arylcarbonyloxy, for example $C_6$–$C_{10}$-arylcarbonyloxy such as benzoyloxy; or aralkylcarbonyloxy, for example $C_6$ to $C_{10}$-aryl-$C_1$–$C_4$-alkylcarbonyloxy such as benzylcarbonyloxy or phenylethylcarbonyloxy. Preferably acyloxy is $C_1$–$C_4$-alkylcarbonyloxy.

"Halogen" as used herein may be fluorine, chlorine, bromine or iodine; preferably it is fluorine, chlorine or bromine.

$Ar^1$ as substituted phenyl may be, for example phenyl substituted by one, two or three substituents, preferably one or two substituents, preferably selected from fluorine, chlorine, bromine, nitro, and cyano-$C_1$–$C_4$-alkyl, especially fluorine or chlorine. When there is one substituent, it is preferably para to the indicated ether group. When there is more than one substituent, preferably one is para to the indicated ether group.

$Ar^2$ as substituted phenyl may, for example, be substituted by one, two, three, four or five, preferably by one, two or three, substituents as hereinbefore described. $Ar^2$ may be, for example, monosubstituted phenyl in which the substituent, preferably halogen, cyano, nitro or $C_1$–$C_4$-alkoxy, is preferably ortho or meta to the indicated —CH═CH— group. $Ar^2$ may alternatively be, for example, disubstituted phenyl in which the substituents are preferably selected from halogen, cyano, hydroxy, nitro, $C_1$–$C_4$-alkoxy, $C_1$–$C_4$-alkyl and $C_1$–$C_4$-haloalkyl, especially one halogen and one $C_1$–$C_4$-alkoxy, or one cyano and one $C_1$–$C_4$-alkoxy. $Ar^2$ may alternatively be, for example, trisubstituted phenyl in which the substituents are preferably selected from halogen, hydroxy, $C_1$–$C_4$-alkoxy and $C_1$–$C_4$-alkoxycarbonyl, or penta-substituted phenyl in which the substituents are preferably halogen, especially fluorine. Especially preferred groups $Ar^2$ are disubstituted phenyl where one substituent is $C_1$–$C_4$-alkoxy, preferably ortho to the —CH═CH— group, and the other, preferably para to the $C_1$–$C_4$-alkoxy group, is halogen, especially chlorine or bromine, or cyano.

$R^1$ as substituted $C_1$–$C_8$-alkyl is preferably substituted $C_1$–$C_4$-alkyl, especially substituted methyl or ethyl. When $R^1$ is $C_1$–$C_8$-alkyl substituted by a cyclic organic group, the latter may be a carbocyclic or heterocyclic group, for example a $C_3$–$C_{15}$-carbocyclic group or a 5- to 7-membered heterocyclic group having one or more, preferably one, two or three, ring hetero atoms selected from nitrogen, oxygen and sulfur. The $C_3$–$C_{15}$-carbocyclic group may be, for example, a cycloaliphatic group having 3 to 8 carbon atoms, preferably $C_5$- or $C_6$-cycloalkyl such as cyclopentyl, methylcyclopentyl or cyclohexyl. The $C_3$–$C_{15}$-carbocyclic group may alternatively be, for example, a $C_6$–$C_{15}$ aromatic group, such as phenyl, which is unsubstituted or substituted by $C_1$–$C_8$-alkyl, $C_1$–$C_8$-alkoxy, halogen, cyano, —CON($R^4$)$R^5$, —SO$_2$N($R^4$)$R^5$ or $C_1$–$C_8$-alkylsulfonylamino where $R^4$ and $R^5$ are as hereinbefore defined. The heterocyclic group may have one nitrogen, oxygen or sulfur atom in the ring or it may have two nitrogens, or one oxygen and one or two nitrogens, or one sulfur and one or two nitrogens in the ring. The heterocyclic group is preferably a heterocyclic aromatic group, for example a 5- or 6-membered heterocyclic group such as furyl, imidazolyl, thiazolyl or pyridyl.

When $R^1$ is $C_1$–$C_4$-alkyl substituted by —CON($R^4$)$R^5$, by way of example $R^4$ and $R^5$ may each be hydrogen or $C_1$–$C_8$-alkyl, or $R^4$ may be hydrogen and $R^5$ may be $C_1$–$C_8$-alkyl, or $R^4$ may be hydrogen or $C_1$–$C_8$-alkyl and $R^5$ may be $C_1$–$C_8$-alkyl substituted by hydroxy or phenyl, or $R^5$ may be phenyl or phenyl substituted by $C_1$–$C_4$-alkyl, $C_1$–$C_4$-alkoxy, halogen or cyano, or $R^4$ and $R^5$ together with nitrogen atom to which they are attached denote a 5-or 6-membered heterocyclic group which may have, for example, 2 ring nitrogen atoms or one ring nitrogen atom and one ring oxygen atom, such as a pyrrolidinyl, pyrrolinyl, pyrazolidinyl, imidazolinyl, piperidinyl, piperazinyl or morpholino group, preferably a saturated heterocyclic group, optionally substituted by at least one $C_1$–$C_8$-alkyl.

Preferred compounds of formula I in free or salt form include those in which
$Ar^1$ is phenyl which is substituted by one or two substituents selected from halogen, nitro, or $C_1$–$C_4$-alkyl optionally substituted by cyano, one of said substituents preferably being para to the indicated ether group,
$Ar^2$ is phenyl substituted by one or two substituents selected from $C_1$–$C_4$-alkoxy, halogen and cyano,
$R^1$ is $C_1$–$C_4$-alkyl substituted by hydroxy, $C_1$–$C_4$-alkoxy, carboxy, —CON($R^4$)$R^5$ where $R^4$ and $R^5$ are each independently $C_1$–$C_4$-alkyl, or a 5- to 7-membered heterocyclic group having one, two or three ring hetero atoms selected from nitrogen, oxygen and sulfur, and
n is 1 or 2.

Preferred compounds of formula I in free or salt form also include those in which
$Ar^1$ is phenyl which is substituted by one or two substituents selected from halogen, nitro, or $C_1$–$C_4$-alkyl optionally substituted by cyano, one of said substituents preferably being para to the indicated ether group,
$Ar^2$ is phenyl substituted by one or two substituents selected from $C_1$–$C_4$-alkoxy, halogen and cyano,
$R^1$ is $C_1$–$C_4$-alkyl substituted by —CON($R^4$)$R^5$ where $R^4$ is hydrogen or $C_1$–$C_4$-alkyl and $R^5$ is phenyl or $C_1$–$C_4$-alkyl optionally substituted by hydroxy, or $R^4$ and $R^5$ together with the nitrogen atom to which they are attached denote a 6-membered heterocyclic group, or by —N($R^2$)$R^3$ where $R^2$ is hydrogen and $R^3$ is $C_1$–$C_8$-alkylcarbonyl or —SO$_2$$R^6$ where $R^6$ is $C_1$–$C_8$-alkyl or $C_1$–$C_8$-haloalkyl, and
n is 1 or 2.

Further preferred compounds of formula I in free or salt form include those in which
$Ar^1$ is phenyl which is substituted by fluorine or chlorine para to the indicated ether group and optionally substituted by one further substituent selected from fluorine or chlorine,
$Ar^2$ is phenyl which is substituted ortho to the indicated —CH═CH— group by $C_1$–$C_4$-alkoxy and para to the $C_1$–$C_4$-alkoxy group by halogen, especially bromine or chlorine, or cyano,
$R^1$ is $C_1$–$C_4$-alkyl substituted by hydroxy, $C_1$–$C_4$-alkoxy, carboxy, —CON($R^4$)$R^5$ where $R^4$ and $R^5$ are each independently $C_1$–$C_4$-alkyl, or a 5- or 6-membered heterocyclic aromatic group having one or two ring nitrogen atoms, and
n is 1.

Further preferred compounds of formula I in free or salt form also include those in which
$Ar^1$ is phenyl which is substituted by fluorine or chlorine para to the indicated ether group and optionally substituted by one further substituent selected from fluorine or chlorine,
$Ar^2$ is phenyl which is substituted ortho to the indicated —CH═CH— group by $C_1$–$C_4$-alkoxy and para to the $C_1$–$C_4$-alkoxy group by halogen, especially bromine or chlorine, or cyano,
$R^1$ is (a) $C_1$–$C_4$-alkyl substituted by —CON($R^4$)$R^5$ where $R^4$ is hydrogen or methyl and $R^5$ is phenyl, $C_1$–$C_4$-alkyl or hydroxy-substituted straight chain $C_1$–$C_4$-alkyl, or $R^4$ and $R^5$ together with the nitrogen atom to which they are attached denote a 6-membered heterocyclic group, preferably saturated, having 2 ring nitrogen atoms or 1 ring nitrogen atom and 1 ring oxygen atom, or (b) $C_1$–$C_4$-alkyl substituted by —N($R^2$)$R^3$ where $R^2$ is hydrogen and $R^3$ is —SO$_2$$R^6$ where $R^6$ is $C_1$–$C_4$-alkyl or $C_1$–$C_4$-haloalkyl, and
n is 1.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

The carbon atom to which $R^1$ is attached in formula I is asymmetric, so the compounds of formula I exist in individual optically active isomeric forms or as mixtures thereof, e.g. as racemic or diastereomeric mixtures. The invention embraces both individual optically active R and S isomers as well as mixtures, e.g. racemic or diastereomeric mixtures, thereof.

Specific especially preferred compounds of the invention are those described hereinafter in the Examples.

The invention also provides a process for the preparation of compounds of formula I which comprises (i) (A) reacting a compound of formula

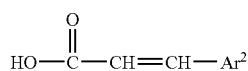

II or an amide-forming derivative thereof, where $Ar^1$, $Ar^2$, $R^1$ and n are as hereinbefore defined, with a compound of formula

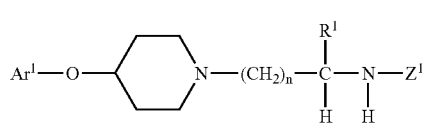

III where $Ar^1$, $R^1$ and n are as hereinbefore defined and $Z^1$ denotes a solid phase substrate chemically linked to the indicated nitrogen atom, and detaching the resulting product from the substrate to replace $Z^1$ by hydrogen; or (B) reacting a compound of formula II or an amide-forming derivative thereof with a compound of formula

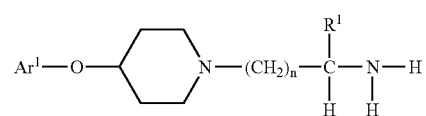

IIIA where $Ar^1$ and $R^1$ are as hereinbefore defined, or (C) where $R^1$ is $C_1$–$C_8$-alkyl substituted by carboxy, reacting a compound of formula I where $R^1$ is $C_1$–$C_8$-alkyl substituted by phenyl-$C_1$–$C_8$-alkoxycarbonyl to convert the phenyl-$C_1$–$C_8$-alkoxycarbonyl to carboxy, or (D) where $R^1$ is $C_1$–$C_8$-alkyl substituted by —CON($R^4$)$R^5$, appropriately amidating a compound of formula I where $R^1$ is $C_1$–$C_8$-alkyl substituted by carboxy, or (E) where $R^1$ is $C_1$–$C_8$-alkyl substituted by —N($R^2$)$R^3$ where $R^2$ is hydrogen and $R^3$ is acyl or —SO$_2$R$^6$, appropriately acylating or sulphonylating respectively a compound of formula I where $R^1$ is $C_1$–$C_8$-alkyl substituted by amino, and (ii) recovering the product in free or salt form.

Process variant (A) may be effected using known methods, or analogously as described hereinafter in the Examples, for example by reacting the substrate-bound compound with the free acid under known peptide coupling conditions, for example in the presence of a tertiary amine and a peptide coupling agent such as a phosphonium salt, a uronium salt such as O-(7-azabenzotriazol-1-yl)-N,N,N$^1$,N$^1$-tetramethyluronium hexafluorophosphate, or diisopropyl-carbodiimide. The reaction may be effected in an inert organic solvent such as dimethyl-formamide (DMF). Suitable reaction temperatures are from 0 to 40° C., e.g. 15 to 25° C. The product may be detached from the substrate in a known manner, for example, where the N atom is linked to a CH$_2$ of a benzyl group in $Z^1$, by treatment with trifluoroacetic acid (TFA).

Process variant (B) may be carried out by known methods or analogously as described hereinafter in the Examples. Conveniently it is effected analogously to the coupling step of process variant (A) as hereinbefore described.

Process variant (C) may be effected using known methods such as alkaline hydrolysis, e.g. in an aqueous alcoholic solvent as described hereinafter in the Examples. The reaction temperature may be, for example, from 10 to 50° C., conveniently ambient temperature.

Process variant (D) may be effected using known methods for amidation of carboxy groups or analogously as described hereinafter in the Examples.

Process variant (E) may be effected using known methods for acylation or sulfonylation of amino groups or analogously as hereinafter described in the Examples.

Compounds of formula II are either available commercially or may be prepared by known methods or analogously as hereinafter described in the Examples.

Compounds of formula III may be prepared by reacting a compound of formula

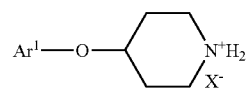

IV where X is the residue of an acid, particularly a carboxylic acid such as trifluoroacetic acid, after removal of an acidic hydrogen atom therefrom, with a compound of formula

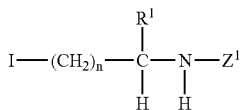
V where $R^1$, $Z^1$ and n are as hereinbefore defined, for example using known procedures such as reaction in an inert organic solvent such as DMF in the presence of a tertiary amine, conveniently at a temperature of 40 to 60° C. Compounds of formula V may be prepared by reaction of a compound of formula

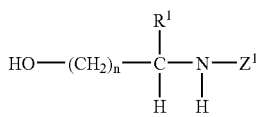
VI where $R^1$, $Z^1$ and n are as hereinbefore defined, with iodine, for example using known procedures such as reaction in an inert organic solvent such as a mixture of THF and acetonitrile in the presence of a triarylphosphine and imidazole, conveniently at a temperature of 10 to 40° C. Compounds of formula VI may be prepared by reaction of a compound of formula

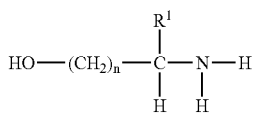
VII where $R^1$ and n are as hereinbefore defined, with a solid phase substrate $Z^1$ having a group, such as an aldehyde group, reactive with amino. Such solid phase substrates, including modified resins, particularly modified polystyrene resins such as a modified polystyrene having a p-formyl-substituted phenoxyalkyl group attached to skeletal benzene rings of the polystyrene, are commercially available. Compounds of formula VII are known or may be prepared by known methods.

Compounds of formula IV may be prepared by reacting a compound of formula $Ar^1OH$ with a compound of formula

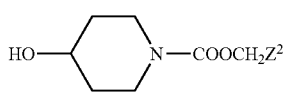
VIII where $Ar^1$ is as hereinbefore defined and $Z^2$ denotes a solid phase substrate chemically linked to the indicated methylene group, diethyldiazodicarboxylate and a triarylphosphine (Mitsunobu reaction), and reacting the resulting product with an acid HX where X is as hereinbefore defined to detach the product from the substrate and replace $COOCH_2Z^2$ by two hydrogen atoms. The reaction is conveniently carried out in an organic solvent, for example an ether such as THF. The Mitsunobu reaction temperature may suitably be from 10–50° C., conveniently room temperature. The product may be detached from the substrate in a known manner, for example by treatment with trifluoroacetic acid.

Compounds of formula VIII may be prepared by reaction of 4-hydroxypiperidine with a compound of formula

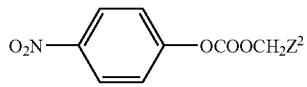
IX where $Z^2$ is as hereinbefore defined. The reaction may suitably be carried out in an inert organic solvent, for example a halohydrocarbon such as dichloromethane (DCM). Suitable reaction temperatures may be from 10–50° C., conveniently room temperature.

Compounds of formula IX may be prepared by reacting p-nitrophenyl chloroformate with a compound of formula $$HOCH_2Z^2 \qquad X$$

where $Z^2$ is as hereinbefore defined. This reaction may be carried out in the presence of a tertiary base such as N-methylmorpholine and in an inert solvent such as DCM. Resin-based compounds of formula X are commercially available, for example as modified polystyrene resins such as Wang resin having a p-hydroxymethyl-substituted phenoxyalkyl group attached to skeletal benzene rings of the polystyrene.

Compounds of formula IIIA may be prepared by reacting a compound of formula IV, or the corresponding free amine, with a compound of formula

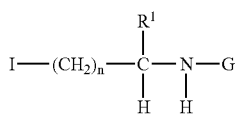
XI where $R^1$ and n are as hereinbefore defined and G is an amine-protecting group, such as a tert-butoxycarbonyl group, for example using known procedures or analogously as described hereinafter in the Examples, such as reaction in an inert organic solvent such as DMF in the presence of a tertiary amine, conveniently at a temperature from ambient to 60° C., followed by removal of the protecting group from the product. Compounds of formula XI are known or may be prepared by known methods, e.g. as described by D. Gani et al, J. Chem. Soc. Perkin Trans. 1, 2513–2525 (1977) or analogously as hereinafter described in the Examples.

In the abovementioned reactions, where it is desired to minimise the possibility of reaction of functional groups other than those participating in the desired reaction, such functional groups may be protected by conventional protecting groups. For example, where $R^1$ is hydroxymethyl or aminomethyl, the hydroxy or amino group in $R^1$ may be protected by a protecting group such as tert-butyl or tert-butoxycarbonyl respectively (a) in the compounds of formulae VII, VI, V and III, which protecting group can be removed by the treatment to remove the product of reaction between compounds of formulae II and III from the solid phase substrate or by a separate reaction, or (b) in the compounds of formulae XI and IIIA, which protecting group can be removed from the reaction product of compounds of formulae II and IIIA, e.g. by catalytic hydrogenolysis, e.g. using ammonium formate and a palladium catalyst as hereinafter described in the Examples.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sone Inc, Second Edition, 1991, which reference also describes procedures suitable for replacement of the protecting groups by hydrogen.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I in free or pharmaceutically acceptable salt form, hereinafter referred to alternatively as agents of the invention, are useful as pharmaceuticals. Accordingly the invention also provides a compound of formula I in free or pharmaceutically acceptable salt form for use as a pharmaceutical. The agents of the invention act as CCR-3 receptor antagonists, thereby inhibiting the infiltration and activation of inflammatory cells, particularly eosinophils, and inhibiting allergic response. The agents of the invention generally exhibit good selectivity for inhibition of CCR-3 relative to inhibition of the α-1 adrenoreceptor. The inhibitory properties of agents of the invention can be demonstrated in the following assay:

CCR-3 Binding Assay

In this assay the effect of agents of the invention on the binding of human eotaxin to human CCR-3 is determined. Recombinant cells expressing human CCR-3 are captured by wheatgerm agglutinin (WGA) polyvinyltoluidene (PVT) SPA beads (available from Amersham), through a specific interaction between the WGA and carbohydrate residues of glycoproteins on the surface of the cells. [$^{125}$I]-human eotaxin (available from Amersham) binds specifically to CCR-3 receptors bringing the [$^{125}$I]-human eotaxin in close proximity to the SPA beads. Emitted â-particles from the [$^{125}$I]-human eotaxin excite, by its proximity, the fluorophore in the beads and produce light. Free [$^{125}$I]-human eotaxin in solution is not in close proximity to the scintillant and hence does not produce light. The scintillation count is therefore a measure of the extent to which the test compound inhibits binding of the eotaxin to the CCR-3.

Preparation of Assay Buffer: 5.96 g HEPES and 7.0 g sodium chloride are dissolved in distilled water and 1M aqueous $CaCl_2$ (1 mL) and 1M aqueous $MgCl_2$ (5 mL) are added. The pH is adjusted to 7.6 with NaOH and the solution made to a final volume of 1 L using distilled water. 5 g bovine serum albumin and 0.1 g sodium azide are then dissolved in the solution and the resulting buffer stored at 4° C. A Complete™ protease inhibitor cocktail tablet (available from Boehringer) is added per 50 mL of the buffer on the day of use.

Preparation of Homogenisation Buffer: Tris-base (2.42 g) is dissolved in distilled water, the pH of the solution is adjusted to 7.6 with hydrochloric acid and the solution is diluted with distilled water to a final volume of 1 L. The resulting buffer is stored at 4° C. A Complete™ protease inhibitor cocktail tablet is added per 50 mL of the buffer on the day of use.

Preparation of membranes: Confluent rat basophil leukemia (RBL-2H3) cells stably expressing CCR3 are removed from tissue culture flasks using enzyme-free cell dissociation buffer and resuspended in phosphate-buffered saline. The cells are centrifuged (800 g, 5 minutes), the pellet resuspended in ice-cold homogenisation buffer using 1 mL homogenisation buffer per gram of cells and incubated on ice for 30 minutes. The cells are homogenised on ice with 10 strokes in a glass mortar and pestle. The homogenate is centrifuged (800 g, 5 minutes, 4° C.), the supernatant further centrifuged (48,000 g, 30 minutes, 4° C.) and the pellet redissolved in Homogenisation Buffer containing 10% (v/v) glycerol. The protein content of the membrane preparation is estimated by the method of Bradford (Anal. Biochem. (1976) 72:248) and aliquots are snap frozen and stored at −80° C.

The assay is performed in a final volume of 250 µL per well of an Optiplate (ex Canberra Packard). To selected wells of the Optiplate are added 50 µL of solutions of a test compound in Assay Buffer containing 5% DMSO (concentrations from 0.01 nM to 10 µM). To determine total binding, 50 µL of the Assay Buffer containing 5% DMSO is added to other selected wells. To determine non-specific binding, 50 µL of 100 nM human eotaxin (ex R&D Systems) in Assay Buffer containing 5% DMSO is added to further selected wells. To all wells are added 50 µL [$^{125}$I]-Human eotaxin (ex Amersham) in Assay Buffer containing 5% DMSO at a concentration of 250 pM (to give a final concentration of 50 pM per well), 50 µL of WGA-PVT SPA beads in Assay Buffer (to give a final concentration of 1.0 mg beads per well) and 100 µL of the membrane preparation at a concentration of 100 µg protein in Assay Buffer (to give a final concentration of 10 µg protein per well). The plate is then incubated for 4 hours at room temperature. The plate is sealed using TopSeal-S (ex Canberra Packard) according to the manufacturer's instructions. The resulting scintillations are counted using a Canberra Packard TopCount, each well being counted for 1 minute. The concentration of test compound at which 50% inhibition occurs ($IC_{50}$) is determined from concentration-inhibition curves in a conventional manner.

The compounds of the Examples hereinbelow have $IC_{50}$ values of the order of 1 µM or less in the above assay. For instance, the compounds of Examples 1, 14 and 16 have $IC_{50}$ values of 16 nM, 11 nM and 2.8 nM respectively.

Having regard to their inhibition of binding of CCR-3, agents of the invention are useful in the treatment of conditions mediated by CCR-3, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis; diseases affecting the nose including acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; inflammatory conditions of the gastrointestinal tract, for example inflammatory bowel disease such as ulcerative colitis and Crohn's disease; and inflammatory conditions of the bone or joint including rheumatoid arthritis, psoriatic arthritis, ankylosing spondylitis and systemic sclerosis.

The agents of the invention may be used in the treatment of other diseases such as multiple sclerosis, atherosclerosis, myasthenia gravis and diabetes (type I).

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49–57; Renzi et al, Am. Rev. Respir. Dis. (1993) 148:932–939; Tsuyuki et al., J. Clin. Invest. (1995) 96:2924–2931; and Cernadas et al (1999) Am. J. Respir. Cell Mol. Biol. 20:1–8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]sulfonyl]ethyl]-amino] ethyl]-2(3H)-benzothiazolone and pharmaceutically acceptable salts thereof (the hydrochloride being Viozan®—AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International Publication No. WO00/75114, which document is incorporated herein by reference, preferably compounds of the Examples thereof, especially a compound of formula

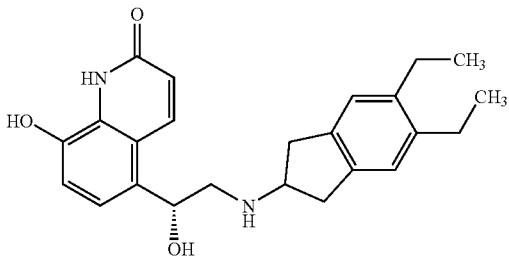

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with other antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO00/66558 (particularly claim 8), and WO00/66559 (particularly claim 9).

In accordance with the foregoing, the invention also provides a method for the treatment of a condition mediated by CCR-3, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition mediated by CCR-3, for example an inflammatory or allergic condition, particularly an inflammatory or obstructive airways disease.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipient and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.01 to 30 mg/kg while for oral administration suitable daily doses are of the order of 0.01 to 100 mg/kg.

The invention is illustrated by the following Examples.

EXAMPLES 1–20

Compounds of formula I which are also of formula

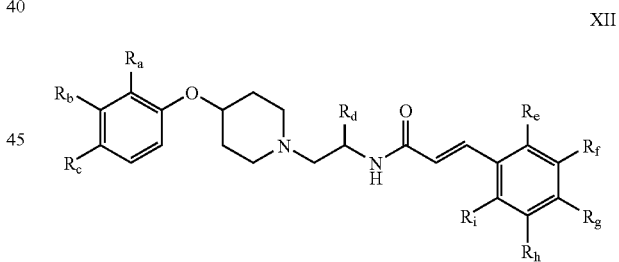

XII are shown in the following table, the method of preparation being described hereinafter. $R_f$, $R_g$ and $R_i$ are each hydrogen in all of the Examples. The table also shows characterising mass spectrometry data and, where the Example is a salt, the identity of the salt-forming acid.

| Example No | $R_a$ | $R_b$ | $R_c$ | $R_d$ | $R_e$ | $R_h$ | M/S | Salt form |
|---|---|---|---|---|---|---|---|---|
| 1 | H | H | F | ⟩―OH | OCH$_3$ | CN | [MH] + 453.9 | CF$_3$CO$_2$H |

-continued
| Example No | $R_a$ | $R_b$ | $R_c$ | $R_d$ | $R_e$ | $R_h$ | M/S | Salt form |
|---|---|---|---|---|---|---|---|---|
| 2 | H | H | F |  | OCH₃ | CN | [MH]+ 468.1 | CF₃COOH |
| 3 | H | H | F |  | OCH₃ | CN | [MH]+ 468.3 | CF₃COOH |
| 4 | H | H | F | 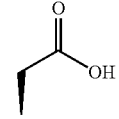 | OCH₃ | CN | [MH]+ 482.1 | — |
| 5 | H | H | F | 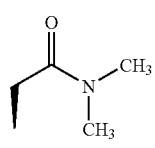 | OCH₃ | CN | [MH]+ 509.1 | CF₃COOH |
| 6 | H | H | F |  | OCH₃ | Cl | [MH]+ 463.0 | CF₃COOH |
| 7 | H | H | F | 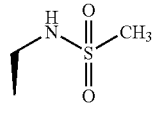 | OCH₃ | CN | [MH]+ 531.0 | CF₃COOH |
| 8 | H | H | F | 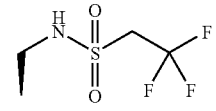 | OCH₃ | CN | [MH]+ 598.9 | CF₃COOH |
| 9 | H | H | F | 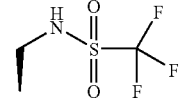 | OCH₃ | CN | [MH]+ 584.7 | CF₃COOH |
| 10 | H | H | F | 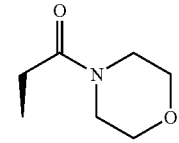 | OCH₃ | CN | [MH]+ 550.5 | CF₃COOH |
| 11 | H | H | F | 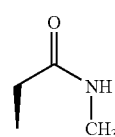 | OCH₃ | CN | [MH]+ 495.1 | CF₃COOH |
| 12 | H | H | F | 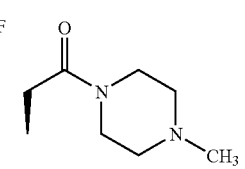 | OCH₃ | CN | [MH]+ 564.1 | CF₃COOH |
| 13 | H | H | F | 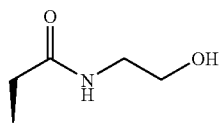 | OCH₃ | CN | [MH]+ 525.1 | CF₃COOH |

-continued

| Example No | R_a | R_b | R_c | R_d | R_e | R_h | M/S | Salt form |
|---|---|---|---|---|---|---|---|---|
| 14 | H | H | F | 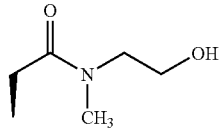 | OCH₃ | CN | [MH] + 537.02 | CF₃COOH |
| 15 | H | H | F | 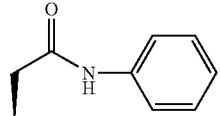 | OCH₃ | CN | [MH] + 557.1 | CF₃COOH |
| 16 | H | H | F | 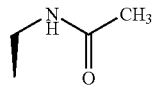 | OCH₃ | CN | [MH] + 495.0 | — |
| 17 | H | Cl | Cl | 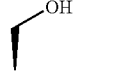 | OCH₃ | CN | [MH] + 504.0 | — |
| 18 | H | H | F | 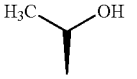 | OCH₃ | Br |  | CF₃COOH |
| 19 | H | H | F | 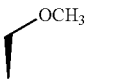 | OCH₃ | Br |  | CF₃COOH |
| 20 | H | H | F | 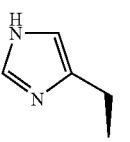 | OCH₃ | CN |  | — |

2-Amino-3-tert-butoxy-propan-1-ol

To a solution of H-D-Ser(C(CH₃)₃)OCH₃ (500 mg, 2.36 mmol) in ether (8 ml) is added a solution of lithium borohydride (2.4 ml, 2M in tetrahydrofuran (THF)) and the suspension stirred at room temperature for 18 hours, after which water (10 ml) is added and the organic phase separated. The aqueous phase is extracted using ether (3×15 ml) and the combined organic extracts dried (MgSO4), filtered and evaporated to give the expected product [MH]⁺ 148.0.

(E)-3-(5-cyano-2-methoxy-phenyl)-acrylic acid

To a suspension of palladium(II)acetate (0.77 g, 3.42 mmol) in N,N-dimethylacetamide (375 ml) are added tetraethylammonium chloride (19.36 g, 114.5 mmol), dicyclohexyl methyl amine (35.1 g, 174.5 mmol), and 3-bromo-4-methoxybenzonitrile (25.51 g, 118.0 mmol) under a nitrogen atmosphere. The suspension is heated to 100–105° C. whereupon t-butyl acrylate (14.82 g, 114.5 mmol) is slowly added over a period of 45 min. After a further 30–60 min stirring at 100° C., the solution is cooled to room temperature and diluted with TBME (375 ml). The resulting biphasic mixture is stirred vigorously for 10 min. The (upper) TBME phase is successively washed with water (100 ml), 10% aq. citric acid (100 ml) and 25% aq. NaCl (100 ml). The combined aqueous phases are extracted with TBME (100 ml). After adding active charcoal (0.4 g), the combined TBME phases are stirred vigorously for 10 min and filtered. Anhydrous Na₂SO₄ (10 g) is added and the resulting suspension is stirred for another 10 min and filtered. The filtrate is concentrated to a volume of 50–70 ml under reduced pressure and, over a period of 25–30 min, added at room temperature to anhydrous trifluoroacetic acid (150 ml). The resulting solution is stirred at room temperature for 60 min (precipitation forms), cooled to 0–5° C. in an ice bath, and diluted with ethyl acetate (410 ml). After stirring vigorously at 0° C. for an additional 60 min, the suspension is filtered. The residue is dried under vacuum at 45–50° C. to give (E)-3-(5-cyano-2-methoxy-phenyl)-acrylic acid as a crystalline solid, mp. 252–253° C. MS (ES): [M-H]⁻ 202.

Example 1

(E)-3-(5-Cyano-2-methoxy-phenyl)-N-{2-[4-(4-fluoro-phenoxy)-piperidin-1-yl]-1-hydroxymethyl-ethyl}-acrylamide To a suspension of 2-(formyl-3-methoxyphenoxy)ethyl polystyrene (AMEBA) resin (ex Novabiochem) (2.13 g, 3.40 mmol) in a mixture of acetic acid/DMF (60 ml, 1:100 v/v) is added 2-amino-3-tert-butoxy-propan-1-ol and sodium triacetoxyborohydride (1.44 g, 6.80 mmol) and the mixture is shaken for 18 hours at 20° C., then filtered. The resin obtained is washed with methanol, DMF and dichloromethane (DCM), then dried under vacuum. A THF/acetonitrile mixture (20 ml, 1:1 v/v) is added to the dried resin followed by iodine (4.30 g, 18.85 mmol), imidazole (1.16 g, 17.00 mmol) and triphenylphosphine (4.46 g, 17.00 mmol). The suspension obtained is shaken for 6 hours at 20° C., then filtered. The resin is washed with THF and dried under vacuum. To the freshly prepared resin obtained (0.30 g, 0.48 mmol) is added a solution of 4-(4-fluoro-phenoxy)-piperidine (309 mg, 1.00 mmol) dissolved in DMF (2 ml) and diisopropylethylamine (62.4 mg, 0.48 mmol). The mixture is heated at 55° C. for 8 hours. The resulting mixture is filtered and the resin is washed with DMF. To the washed resin are added (E)-3-(5-cyano-2-methoxy-phenyl)-acrylic acid (0.27 g, 1.05 mmol), O-(7-azabenzotriazol-1-yl)-N,N,N',N'-tetramethyluroniumhexafluoro-phosphate (547 mg, 1.44 mmol) diisopropylethylamine (186 mg, 1.44 mmol) and DMF (4 ml) and the mixture is shaken at 20° C. for 18 hours, then washed with DMF and methanol, after which it is treated with trifluoroacetic acid/DCM (6 ml, 1:1 v/v) at 20° C. for 1 hour to remove the product from the resin. The resulting mixture is filtered and the filtrate evaporated under vacuum to give the product, [MH]+ 453.9.

Example 14

(R)-3-tert-Butoxycarbonylamino-4-[4-(4-fluoro-phenoxy)-piperidin-1-yl]-butyric acid benzyl ester Triphenylphosphine bound to cross-linked polystyrene resin (2.16 g, mol/g, 6.47 mmol) is suspended in dry DCM (50 ml) at ambient temperature under a nitrogen atmosphere. Iodine (1.64 g, 6.47 mmol) is added and the reaction mixture stirred for 15 minutes. Imidazole (0.50 g, 7.35 mmol) is then added and the reaction mixture is stirred for a further 15 minutes. A solution of (R)-3-.tert.-butoxycarbonylamino-4-hydroxy-butyric acid benzyl ester (prepared as described by D. Gani et al J. Chem. Soc. Perkin Trans. 1, 2513–2525, 1997 (0.909 g, 2.94 mmol) in dry DCM (10 ml) is added and the reaction mixture is stirred at reflux for 1 hour. The polymer is removed by filtration, and the filtrate is first washed with aqueous 5% sodium thiosulphate solution and then water. The organic phase is dried over MgSO$_4$ and evaporated to yield (R)-3-tert-butoxycarbonylamino-4-iodo-butyric acid benzyl ester as a crude oil. A solution of (R)-3-tert-butoxycarbonylamino-4-iodo-butyric acid benzyl ester (1.017 g, 2.43 mmol) and 4-(4-fluoro-phenoxy)-piperidine (0.569 g, 2.916 mmol) in DMF (25 ml) is treated with triethylamine (0.406 ml, 2.916 mmol). The reaction mixture is stirred at ambient temperature for 60 hours, and then partitioned between ethylacetate and water. The ethylacetate phase is dried over MgSO$_4$ and evaporated. The crude product is purified by flash silica chromatography (elution with 2:1 hexane/ethylacetate) to afford (R)-3-tert-butoxycarbonylamino-4-[4-(4-fluoro-phenoxy)-piperidin-1-yl]-butyric acid benzyl ester. [MH]+ 487.1.

(R)-3-Amino-4-[4-(4-fluoro-phenoxy)-piperidin-1-yl]-butyric acid benzyl ester

A solution of (R)-3-tert-butoxycarbonylamino-4-[4-(4-fluoro-phenoxy)-piperidin-1-yl]-butyric acid benzyl ester (0.488 g, 1.0 mmol) in DCM (8 ml) is treated with trifluoroacetic acid (2 ml). The reaction mixture is stirred at ambient temperature for 1 hour. The solvent is evaporated and the residue taken up in DCM and washed with saturated aqueous NaHCO$_3$. The organic phase is dried over MgSO$_4$ and evaporated to yield (R)-3-amino-4-[4-(4-fluorophenoxy)-piperidin-1-yl]-butyric acid benzyl ester. [MH]+ 387.1

(R)-3-[(E)3-(5-Cyano-2-methoxy-phenyl)-acryloylamino]-4-[4-(4-fluoro-phenoxy)-piperidin-1-yl]-butyric acid benzyl ester A solution of (E)-3-(5-cyano-2-methoxy-phenyl)-acrylic acid (0.916 g, 4.51 mmol), triethylamine (1.257 ml, 9.02 mmol) and 2-(1H-benzotriazol-1-yl)-1,1,3,3-tetramethyluronium tetrafluoroborate (1.44 g, 4.51 mmol) in DCM (10 ml) is treated with (R)-3-amino-4-[4-(4-fluoro-phenoxy)-piperidin-1-yl]-butyric acid benzyl ester. The reaction mixture is stirred at ambient temperature for 2 hours, then is washed with water, dried over MgSO$_4$ and evaporated. The crude product is purified by flash silica chromatography (elution with 2:1 ethylacetate:hexane) to afford (R)-3-[(E)-3-(5-cyano-2-methoxy-phenyl)-acryloylamino]-4-[4-(4-fluoro-phenoxy)-piperidin-1-yl]-butyric acid benzyl ester. [MH]+ 572.1.

(R)-3-[(E)-3-(5-Cyano-2-methoxy-phenyl)-acryloylamino]-4-[4-(4-fluoro-phenoxy)-piperidin-1-yl]-butyric acid A solution of (R)-3-[(E)-3-(5-cyano-2-methoxy-phenyl)-acryloylamino]-4-[4-(4-fluoro-phenoxy)-piperidin-1-yl]-butyric acid benzyl ester (1.43 g, 2.52 mmol) in methanol (15 ml) is treated with NaOH solution, (2.5 ml, 4M). The reaction mixture is stirred at ambient temperature for 1 hour. The methanol is evaporated and the resulting aqueous solution diluted with water and washed with diethyl ether. The aqueous phase is neutralised with 1N HCl solution and extracted into isopropanol/chloroform (1:3). The organic phase is evaporated and dried under high vacuum to afford (R)-3-[(E)-3-(5-cyano-2-methoxy-phenyl)-acryloylamino]-4-[4-(4-fluoro-phenoxy)-piperidin-1-yl]-butyric acid. [MH]+ 482.1.

(E)-3-(5-Cyano-2-methoxy-phenyl)-N-((R)-2-[4-(4-fluoro-phenoxy)-piperidin-1-yl]-1-{[(2-hydroxy-ethyl)-methyl-carbamoyl]-methyl}-ethyl)-acrylamide—Example 14

A solution of (R)-3-[(E)-3-(5-cyano-2-methoxy-phenyl)-acryloylamino]-4-[4-(4-fluoro-phenoxy)-piperidin-1-yl]-butyric acid (0.1 g, 0.21 mmol) in DMF (1 ml) is treated with diisopropylethylamine (0.108 ml, 0.62 mmol) and 2-methylamino-ethanol (0.02 ml, 0.248 mmol). To the solution is added O-(7-azabenzotriazol-1-yl)-1,1,3,3-tetramethyluroniumhexafluorophosphate (0.117 g, 0.31 mmol) and the reaction mixture stirred at room temperature for 1 hour. The reaction mixture is partioned between ethylacetate and saturated aqueous NaHCO$_3$. The ethylacetate phase is washed with saturated brine, dried over MgSO$_4$ and evaporated. The crude product is purified by flash silica chromatography (elution with 5:95 methanol/DCM) to afford (E)-3-(5-cyano-2-methoxy-phenyl)-.N.-((R)-2-[4-(4-fluoro-phenoxy)-piperidin-1-yl]-1-{[(2-hydroxy-ethyl)-methyl-carbamoyl]-methyl}-ethyl)-acrylamide. [M-H] 537.02.

Example 16

[(R)-1-(tert-Butoxycarbonylamino-methyl)-2-hydroxy-ethyl]-carbamic acid benzyl ester A solution of (R)-2-benzyloxycarbonylamino-3-.tert.-butoxycarbonylamino-propionic acid (0.5 g, 1.47 mmol) in dry THF (5 ml) cooled to 0° C. is treated with N-methylmorpholine (0.16 ml, 1.47 mmol) and isobutylchloroformate (0.2 ml, 1.47 mmol). The reaction mixture is stirred at 0° C. for 15 minutes then added to a vigorously stirred suspension of sodium borohydride (0.16 g, 4.41 mmol) in dry tetrahydrofuran (5 ml) at 0° C. The reaction mixture is stirred for a further 2 hours, then quenched with water. The THF is evaporated and the remaining aqueous solution extracted into ethylacetate. The ethylacetate is washed with brine, dried over MgSO$_4$ and evaporated to dryness. The crude product is purified by flash silica chromatography (elution with hexane:ethylacetate, 1:1) to afford [(R)-1-(tert-butoxycarbonylamino-methyl)-2-hydroxy-ethyl]-carbamic acid benzyl ester. [MH]+ 325.1

[(R)-1-(tert-Butoxycarbonylamino-methyl)-2-iodo-ethyl]-carbamic acid benzyl ester Triphenylphosphine bound to cross-linked polystyrene resin (0.82 g, 3 mmol/g, 2.47 mmol) is suspended in dry DCM (10 ml) at ambient temperature under a nitrogen atmosphere. Iodine (0.62 g, 2.47 mmol) is added and the reaction mixture stirred for 15 minutes. Imidazole (0.167 g, 2.47 mmol) is then added and the reaction mixture is stirred for a further 15 minutes. A solution of [(R)-1-(tert-butoxycarbonylamino-methyl)-2-hydroxy-ethyl]-carbamic acid benzyl ester (0.401 g, 1.23 mmol) in dry dichloromethane (5 ml) is added and the reaction mixture is stirred at reflux for 1.5 hour. The polymer is removed by filtration, and the filtrate is first washed with aqueous 5% sodium thiosulphate solution and then water. The organic phase is dried over MgSO$_4$ and evaporated to yield [(R)-1-(tert-butoxycarbonylamino-methyl)-2-iodo-ethyl]-carbamic acid benzyl ester. [MH]+ 435.0.

{(R)-1-(tert-Butoxycarbonylamino-methyl)-2-[4-(4-fluoro-phenoxy)-piperidin-1-yl]-ethyl}-carbamic acid benzyl ester A solution of [(R)-1-(tert-butoxycarbonylamino-methyl)-2-iodo-ethyl]-carbamic acid benzyl ester (0.61 g, 1.2 mmol) and 4-(4-fluoro-phenoxy)-piperidine (0.24 g, 1.23 mmol) in dichloromethane (5 ml) is treated with triethylamine (0.335 ml, 2.46 mmol). The reaction mixture is stirred at ambient temperature for 5 days, the solvent evaporated and the residue partitioned between ethylacetate and saturated aqueous NaHCO$_3$. The ethylacetate phase is washed with brine, dried over MgSO$_4$ and evaporated. The crude product is purified by flash silica chromatography (elution with 4:1 hexane/ethylacetate) to afford {(R)-1-(tert-butoxycarbonylamino-methyl)-2-[4-(4-fluoro-phenoxy)-piperidin-1-yl]-ethyl}-carbamic acid benzyl ester [MH]$^+$ 502.2.

{(R)-2-Amino-3-[4-(4-fluoro-phenoxy)-piperidin-1-yl]-propyl}-carbamic acid tert-butyl ester A solution of {(R)-1-(tert-butoxycarbonylamino-methyl)-2-[4-(4-fluoro-phenoxy)-piperidin-1-yl]-ethyl}-carbamic acid benzyl ester (0.88 g, 1.77 mmol) and ammonium formate (0.33 g, 5.31 mmol) in methanol is treated with 10% palladium on charcoal (0.3 g). The reaction mixture is stirred at ambient temperature for 1 hour under nitrogen and then is filtered and evaporated. The residue is dissolved in ethylacetate and washed with saturated brine. The ethylacetate phase is dried over MgSO$_4$ and evaporated to afford {(R)-2-amino-3-[4-(4-fluoro-phenoxy)-piperidin-1-yl]-propyl}-carbamic acid tert-butyl ester. [MH]$^+$ 368.1.

{(R)-2-[(E)-3-(5-Cyano-2-methoxy-phenyl)-acryloylamino]-3-[4-(4-fluoro-phenoxy)-piperidin-1-yl]-propyl}-carbamic add tert-butyl ester A solution of (E)-3-(5-cyano-2-methoxy-phenyl)-acrylic acid (0.36 g, 1.77 mmol), 2-(1H-benzotriazol-1-yl)-1,1,3,3-tetramethyl-uronium tetrafluoroborate (1.01 g, 2.65 mmol) and diisopropylethylamine (0.46 ml, 2.65 mmol) in DCM (15 ml) is treated with a solution of {(R)-2-Amino-3-[4-(4-fluoro-phenoxy)-piperidin-1-yl]-propyl}-carbamic acid .tert.-butyl ester (0.65 g, 1.77 mmol) in DCM (5 ml). The reaction mixture is stirred at ambient temperature for 30 minutes, then washed with saturated aqueous NaHCO$_3$, water and brine. The DCM phase is dried over MgSO$_4$ and evaporated. The crude product is purified by flash silica chromatography (elution with 2% methanol in DCM) to afford {(R)-2-[(E)-3-(5-cyano-2-methoxy-phenyl)-acryloylamino]-3-[4-(4-fluoro-phenoxy)-piperidin-1-yl]-propyl}-carbamic acid tert-butyl ester. [MH]$^+$ 553.0.

(E)-N-{(R)-1-Aminomethyl-2-[4-(4-fluoro-phenoxy)-piperidin-1-yl]-ethyl}-3-(5-cyano-2-methoxy-phenyl)-acrylamide.HCl salt A solution of {(R)-2-[(E)-3-(5-cyano-2-methoxy-phenyl)-acryloylamino]-3-[4-(4-fluoro-phenoxy)-piperidin-1-yl]-propyl}-carbamic acid tert-butyl ester (0.39 g, 0.71 mmol) in DCM (2 ml) is treated with 4M hydrogen chloride in dioxane (1 ml). The reaction mixture is stirred at room temperature for 1.5 hours and then the solvent evaporated. The residue is co-evaporated with ethanol (×2) to afford (E)-N-{(R)-1-aminomethyl-2-[4-(4-fluoro-phenoxy)-piperidin-1-yl]-ethyl}-3-(5-cyano-2-methoxy-phenyl)-acrylamide.HCl salt. [MH]+ 453.2.

(E)-N-{(R)-1-(Acetylamino-methyl)-2-[4-(4-fluoro-phenoxy)-piperidin-1-yl]-ethyl}-3-(5-cyano-2-methoxy-phenyl)-acrylamide—Example 16

A solution of E)-N-{(R)-1-aminomethyl-2-[4-(4-fluoro-phenoxy)-piperidin-1-yl]-ethyl}-3-(5-cyano-2-methoxy-phenyl)-acrylamide.HCl salt (0.35 g, 0.66 mmol) and triethylamine (0.27 ml, 1.99 mmol) in DCM (5 ml) is treated with acetyl chloride (0.042 ml, 0.6 mmol) at 5° C. The reaction mixture is stirred at ambient temperature for 1 hour then washed with water, saturated aqueous NaHCO$_3$ and brine. The organic phase is dried over MgSO$_4$ and the solvent evaporated. The crude product is purified by flash chromatography (elution methanol:DCM; 4:96) to afford (E)-N-{(R)-1-(acetylamino-methyl)-2-[4-(4-fluoro-phenoxy)-piperidin-1-yl]-ethyl}-3-(5-cyano-2-methoxy-phenyl)-acrylamide. [MH]+ 495.0.

The compounds of Examples 2 to 13 and 15 are prepared by procedures analogous to the appropriate Example procedures above, using appropriate starting materials.

The invention claimed is:
1. A compound of formula I

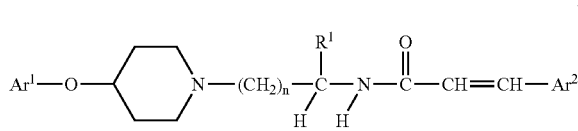

in free or salt form, where

Ar¹ is phenyl substituted by one or more substituents selected from halogen, cyano, nitro, and $C_1$–$C_8$-alkyl optionally substituted by cyano or halogen;

Ar² is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl;

R¹ is $C_1$–$C_8$-alkyl substituted by hydroxy, $C_1$–$C_8$-alkoxy, acyloxy, —N(R²)R³, halogen, carboxy, $C_1$–$C_8$-alkoxycarbonyl, phenyl-$C_1$–$C_8$-alkoxycarbonyl, —CON(R⁴)R⁵ or by a $C_3$–$C_{15}$-carbocyclic group or a 5- to 7-membered heterocyclic group that contains at least one ring heteroatom selected from the group consisting of nitrogen, oxygen and sulphur;

R² and R³ are each independently hydrogen or $C_1$–$C_8$-alkyl, or R² is hydrogen and R³ is acyl or —SO₂R⁶, or R² and R³ together with the nitrogen atom to which they are attached denote a 5- or 6-membered heterocyclic group;

R⁴ and R⁵ are each independently hydrogen, $C_1$–$C_8$-alkyl optionally substituted by hydroxy or phenyl, or phenyl optionally substituted by $C_1$–$C_8$-alkyl, halogen, cyano or $C_1$–$C_8$-alkoxy, or R⁴ and R⁵ together with the nitrogen atom to which they are attached denote a 5- or 6-membered heterocyclic group;

R⁶ is $C_1$–$C_8$-alkyl, $C_1$–$C_8$-haloalkyl, or phenyl optionally substituted by $C_1$–$C_8$-alkyl; and n is 1, 2, 3 or 4.

2. A compound of formula

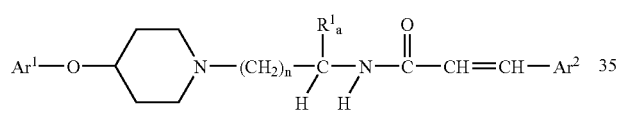

IA in free or salt form, where

Ar¹ is phenyl substituted by one or more substituents selected from halogen, cyano, nitro, and $C_1$–$C_8$-alkyl optionally substituted by cyano or halogen;

Ar² is phenyl or naphthyl which is unsubstituted or substituted by one or more substituents selected from halogen, cyano, hydroxy, nitro, $C_1$–$C_8$-alkyl, $C_1$–$C_8$-haloalkyl, $C_1$–$C_8$-alkoxy or $C_1$–$C_8$-alkoxycarbonyl;

$R^1_a$ is $C_1$–$C_8$-alkyl substituted by hydroxy, $C_1$–$C_8$-alkoxy, acyloxy, N(R²)R³, halogen, carboxy, $C_1$–$C_8$-alkoxycarbonyl, —CON(R⁴)R⁵ or by a $C_3$–$C_{15}$-carbocyclic group or a 5- to 7-membered heterocyclic group that contains at least one ring heteroatom selected from the group consisting of nitrogen, oxygen and sulphur;

R² and R³ are each independently hydrogen or $C_1$–$C_8$-alkyl, or R² is hydrogen and R³ is acyl or —SO₂R⁶, or R² and R³ together with the nitrogen atom to which they are attached denote a 5- or 6-membered heterocyclic group;

R⁴ and R⁵ are each independently hydrogen or $C_1$–$C_8$-alkyl, or R⁴ and R⁵ together with the nitrogen atom to which they are attached denote a 5- or 6-membered heterocyclic group;

R⁶ is $C_1$–$C_8$-alkyl, $C_1$–$C_8$-haloalkyl, or phenyl optionally substituted by $C_1$–$C_8$-alkyl; and n is 1, 2, 3 or 4.

3. A compound according to claim 1, in which Ar² is monosubstituted phenyl in which the substituent is halogen, cyano, nitro or $C_1$–$C_4$-alkoxy; or disubstituted phenyl in which the substituents are selected from halogen, cyano, hydroxy, nitro, $C_1$–$C_4$-alkoxy, $C_1$–$C_4$-alkyl and $C_1$–$C_4$-haloalkyl; or trisubstituted phenyl in which the substituents are selected from halogen, hydroxy, $C_1$–$C_4$-alkoxy and $C_1$–$C_4$-alkoxycarbonyl; or penta-substituted phenyl in which the substituents are halogen.

4. A compound according to claim 1, in which

Ar¹ is phenyl which is substituted by one or two substituents selected from halogen, nitro, or $C_1$–$C_4$-alkyl optionally substituted by cyano, one of said substituents being para to the indicated ether group;

Ar² is phenyl substituted by one or two substituents selected from $C_1$–$C_4$-alkoxy, halogen and cyano;

R¹ is $C_1$–$C_4$-alkyl substituted by hydroxy, $C_1$–$C_4$-alkoxy, carboxy, —CON(R⁴)R⁵ where R⁴ and R⁵ are each independently $C_1$–$C_4$-alkyl, or a 5- to 7-membered heterocyclic group having one, two or three ring hetero atoms selected from nitrogen, oxygen and sulfur; and n is 1 or 2.

5. A compound according to claim 1, in which

Ar¹ is phenyl which is substituted by one or two substituents selected from halogen, nitro, or $C_1$–$C_4$-alkyl optionally substituted by cyano, one of said substituents preferably being para to the indicated ether group;

Ar² is phenyl substituted by one or two substituents selected from $C_1$–$C_4$-alkoxy, halogen and cyano;

R¹ is $C_1$–$C_4$-alkyl substituted by —CON(R⁴)R⁵ where R⁴ is hydrogen or $C_1$–$C_4$-alkyl and R⁵ is phenyl or $C_1$–$C_4$-alkyl optionally substituted by hydroxy, or R⁴ and R⁵ together with the nitrogen atom to which they are attached denote a 6-membered heterocyclic group, or by —N(R²)R³ where R² is hydrogen and R³ is $C_1$–$C_8$-alkylcarbonyl or —SO₂R⁶ where R⁶ is $C_1$–$C_8$-alkyl or $C_1$–$C_8$-haloalkyl; and n is 1 or 2.

6. A compound according to claim 1, in which

Ar¹ is phenyl which is substituted by fluorine or chlorine para to the indicated ether group and optionally substituted by one further substituent selected from fluorine or chlorine;

Ar² is phenyl which is substituted ortho to the indicated —CH=CH— group by $C_1$–$C_4$-alkoxy and para to the $C_1$–$C_4$-alkoxy group by halogen, especially bromine or chlorine, or cyano;

R¹ is $C_1$–$C_4$-alkyl substituted by hydroxy, $C_1$–$C_4$-alkoxy, carboxy, —CON(R⁴)R⁵ where R⁴ and R⁵ are each independently $C_1$–$C_4$-alkyl, or a 5- or 6-membered heterocyclic aromatic group having one or two ring nitrogen atoms; and n is 1.

7. A compound according to claim 1, in which

Ar¹ is phenyl which is substituted by fluorine or chlorine para to the indicated ether group and optionally substituted by one further substituent selected from fluorine or chlorine;

Ar² is phenyl which is substituted ortho to the indicated —CH=CH— group by $C_1$–$C_4$-alkoxy and para to the $C_1$–$C_4$-alkoxy group by halogen, especially bromine or chlorine, or cyano;

R¹ is (a) $C_1$–$C_4$-alkyl substituted by —CON(R⁴)R⁵ where R⁴ is hydrogen or methyl and R⁵ is phenyl, $C_1$–$C_4$-alkyl or hydroxy-substituted straight chain $C_1$–$C_4$-alkyl, or R⁴ and R⁵ together with the nitrogen atom to which they are attached denote a 6-membered heterocyclic group having 2 ring nitrogen atoms or 1 ring nitrogen atom and 1 ring oxygen atom, or (b) $C_1$–$C_4$-alkyl substituted by —N(R²)R³ where R² is hydrogen and R³ is C₁–C₄-alkylcarbonyl or —SO₂R⁶ where R⁶ is C₁–C₄-alkyl or C₁–C₄-haloalkyl; and
n is 1.

8. A compound according to claim 1 which is of formula

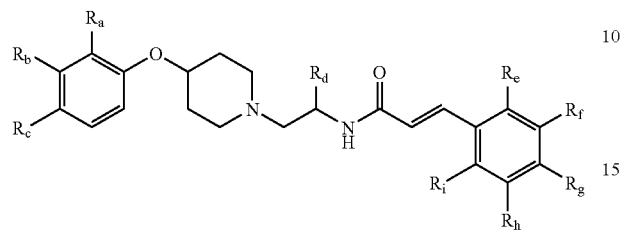

XII in free or pharmaceutically acceptable salt form, where $R_a$, $R_b$, $R_c$, $R_d$, $R_e$ and $R_h$ are as shown in the following table:

| $R_a$ | $R_b$ | $R_c$ | $R_d$ | $R_e$ | $R_h$ |
|---|---|---|---|---|---|
| H | H | F | CH₂OH | OCH₃ | CN |
| H | H | F | CH(CH₃)OH | OCH₃ | CN |
| H | H | F | CH₂OCH₃ | OCH₃ | CN |
| H | H | F | CH₂C(O)OH | OCH₃ | CN |
| H | H | F | CH₂C(O)N(CH₃)₂ | OCH₃ | CN |
| H | H | F | CH₂OH | OCH₃ | Cl |
| H | H | F | CH₂NHS(O)₂CH₃ | OCH₃ | CN |
| H | H | F | CH₂NHS(O)₂CH₂CF₃ | OCH₃ | CN |
| H | H | F | CH₂NHS(O)₂CF₃ | OCH₃ | CN |
| H | H | F | CH₂C(O)-morpholinyl | OCH₃ | CN |
| H | H | F | CH₂C(O)NHCH₃ | OCH₃ | CN |
| H | H | F | CH₂C(O)-N-methylpiperazinyl | OCH₃ | CN |
| H | H | F | CH₂C(O)NHCH₂CH₂OH | OCH₃ | CN |
| H | H | F | CH₂C(O)N(CH₃)CH₂CH₂OH | OCH₃ | CN |
| H | H | F | CH₂C(O)NHPh | OCH₃ | CN |
| H | H | F | CH₂NHC(O)CH₃ | OCH₃ | CN |
| H | Cl | Cl | CH₂OH | OCH₃ | CN |
| H | H | F | CH(CH₃)OH | OCH₃ | Br |
| H | H | F | CH₂OCH₃ | OCH₃ | Br |
| H | H | F | CH₂-imidazolyl | OCH₃ | CN | and $R_f$, $R_g$ and $R_i$ are each hydrogen.

9. A compound according to claim 2, in which Ar² is monosubstituted phenyl in which
the substituent is halogen, cyano, nitro or C₁–C₄-alkoxy; or disubstituted phenyl in which the substituents are selected from halogen, cyano, hydroxy, nitro, $C_1$–$C_4$-alkoxy, $C_1$–$C_4$-alkyl and $C_1$–$C_4$-haloalkyl; or trisubstituted phenyl in which the substituents are selected from halogen, hydroxy, $C_1$–$C_4$-alkoxy and $C_1$–$C_4$-alkoxy-carbonyl; or penta-substituted phenyl in which the substituents are halogen.

10. A pharmaceutical composition comprising as active ingredient a compound according to claim 1, optionally together with a pharmaceutically acceptable diluent or carrier therefor.

11. A pharmaceutical composition comprising as active ingredient a compound according to claim 2, optionally together with a pharmaceutically acceptable diluent or carrier therefor.

12. A pharmaceutical composition comprising as active ingredient a compound according to claim 8, optionally together with a pharmaceutically acceptable diluent or carrier therefor.

13. A method of treating asthma, in a subject in need of such treatment, which comprises administering to said subject an effective amount of a compound of formula I as defined in claim 1.

14. A method of treating asthma, in a subject in need of such treatment, which comprises administering to said subject an effective amount of a compound of formula XII as defined in claim 8.

15. A method of treating asthma, in a subject in need of such treatment, which comprises administering to said subject an effective amount of a compound of formula IA as defined in claim 2.

16. A process for the preparation of a compound of formula I, as defined in claim 1, which comprises (i) (A) reacting a compound of formula

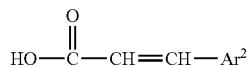

II where $Ar^2$ is as defined in claim 1, with a compound of formula

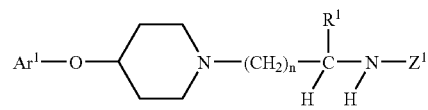

III where $Ar^1$, $R^1$ and n are as defined in claim 1 and $Z^1$ denotes a solid phase substrate chemically linked to the indicated nitrogen atom, and detaching the resulting product from the substrate to replace $Z^1$ by hydrogen; or (B) reacting a compound of formula II with a compound of formula

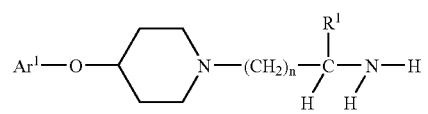

IIIA where $Ar^1$ and $R^1$ are as defined in claim 1; or (C) where $R^1$ is $C_1$–$C_8$-alkyl substituted by carboxy, reacting a compound of formula I where $R^1$ is $C_1$–$C_8$-alkyl substituted by phenyl-$C_1$–$C_8$-alkoxy-carbonyl to convert the phenyl-$C_1$–$C_8$-alkoxycarbonyl to carboxy; or (D) where $R^1$ is $C_1$–$C_8$-alkyl substituted by —CON($R^4$)$R^5$, appropriately amidating a compound of formula I where $R^1$ is $C_1$–$C_8$-alkyl substituted by carboxy; or (E) where $R^1$ is $C_1$–$C_8$-alkyl substituted by —N($R^2$)$R^3$ where $R^2$ is hydrogen and $R^3$ is acyl or —SO$_2$R$^6$, appropriately acylating or sulphonylating respectively a compound of formula I where $R^1$ is $C_1$–$C_8$-alkyl substituted by amino; and (ii) recovering the product in free or salt form.

* * * * *